United States Patent
Schneider et al.

(10) Patent No.: US 10,123,781 B2
(45) Date of Patent: Nov. 13, 2018

(54) AUTOMATED SEGMENTATION OF TRI-PLANE IMAGES FOR REAL TIME ULTRASONIC IMAGING

(71) Applicant: KONINKLIJKE PHILIPS N.V., Eindhoven (NL)

(72) Inventors: Robert Joseph Schneider, Eindhoven (NL); Mary Kay Bianchi, Eindhoven (NL); Robin S. Brooks, Eindhoven (NL); Michael Daniel Cardinale, Eindhoven (NL); David Prater, Eindhoven (NL); Lydia Rivera, V, Eindhoven (NL); Ivan Salgo, Eindhoven (NL); Scott Holland Settlemier, Eindhoven (NL); Jean Margaret Williams, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/032,719

(22) PCT Filed: Nov. 4, 2014

(86) PCT No.: PCT/IB2014/065779
§ 371 (c)(1),
(2) Date: Apr. 28, 2016

(87) PCT Pub. No.: WO2015/068099
PCT Pub. Date: May 14, 2015

(65) Prior Publication Data
US 2016/0249885 A1 Sep. 1, 2016

Related U.S. Application Data

(60) Provisional application No. 61/899,895, filed on Nov. 5, 2013.

(51) Int. Cl.
*G06K 9/00* (2006.01)
*A61B 8/08* (2006.01)
(Continued)

(52) U.S. Cl.
CPC .............. *A61B 8/523* (2013.01); *A61B 5/14* (2013.01); *A61B 8/0883* (2013.01); *A61B 8/145* (2013.01);
(Continued)

(58) Field of Classification Search
CPC ........... A61B 8/08; A61B 8/483; A61B 6/503; A61B 8/0883; A61B 8/12; A61B 8/14;
(Continued)

(56) References Cited

U.S. PATENT DOCUMENTS 5,997,479 A 12/1999 Savord et al.
6,106,466 A * 8/2000 Sheehan ............... A61B 5/1075
128/916

(Continued)

FOREIGN PATENT DOCUMENTS

JP 2006175229 A 7/2006

OTHER PUBLICATIONS

Orderud et al "Automatic Alignment of Standard Views in 3D Echocardiograms Using Real-Time Tracking" Proceedings of SPIE Medical Imaging 2009, vol. 7265 2009 p. 72650D-1-72650D-7.
(Continued)

*Primary Examiner* — Tom Y Lu (57) ABSTRACT

An ultrasonic diagnostic imaging system and method enable the automatic acquisition of standard view planes of the heart in real time, such as the AP4, AP3, and AP2 views. A 3D image of the heart is acquired and the processed in conjunction with a geometrical heart model. The heart model is fitted to the heart in its acquired pose to segment the desired image planes from the 3D image data. During
(Continued)

successive image acquisition intervals the image planes are tracked through successive image data as multi-plane system to update a display of the multiple images. The successive image acquisitions can be volume image acquisitions or multi-plane acquisitions of just the tracked image planes during each acquisition interval.

20 Claims, 4 Drawing Sheets (51) Int. Cl.
      *A61B 8/14*     (2006.01)
      *G01S 15/89*    (2006.01)
      *G01S 7/52*     (2006.01)
      *G01S 15/66*    (2006.01)
      *A61B 5/145*    (2006.01)
      *A61B 8/00*     (2006.01)
      *G06T 7/00*     (2017.01)
      *G06T 7/20*     (2017.01)
      *G06T 7/73*     (2017.01)
      *G06T 7/11*     (2017.01)
      *G06T 7/149*    (2017.01)
      *G06T 7/246*    (2017.01)

(52) U.S. Cl.
CPC ............ *A61B 8/4494* (2013.01); *A61B 8/463* (2013.01); *A61B 8/483* (2013.01); *A61B 8/486* (2013.01); *A61B 8/488* (2013.01); *A61B 8/5276* (2013.01); *G01S 7/52063* (2013.01); *G01S 7/52074* (2013.01); *G01S 15/66* (2013.01); *G01S 15/8925* (2013.01); *G01S 15/8993* (2013.01); *G06T 7/0012* (2013.01); *G06T 7/11* (2017.01); *G06T 7/149* (2017.01); *G06T 7/20* (2013.01); *G06T 7/251* (2017.01); *G06T 7/75* (2017.01); *G06T 2207/10016* (2013.01); *G06T 2207/10136* (2013.01); *G06T 2207/20128* (2013.01); *G06T 2207/30048* (2013.01)

(58) Field of Classification Search
CPC ... A61B 8/4405; A61B 8/4411; A61B 8/4427; A61B 8/461; A61B 8/466; A61B 8/467; A61B 8/523; G06T 2207/10136; G06T 2207/30048; G06T 7/2046; G06T 7/208; G06T 7/251; G06T 7/27
See application file for complete search history.

(56) References Cited

U.S. PATENT DOCUMENTS

| | | |
|---|---|---|
| 6,436,048 B1 | 8/2002 | Pesque |
| 8,094,772 B2 | 1/2012 | Grass et al. |
| 2008/0069436 A1* | 3/2008 | Orderud .................. G06T 7/20 382/154 |
| 2010/0195881 A1 | 8/2010 | Orderud et al. |
| 2010/0249589 A1 | 9/2010 | Lysyansky et al. |
| 2011/0201935 A1* | 8/2011 | Collet-Billon ....... A61B 8/0833 600/443 |
| 2014/0022250 A1* | 1/2014 | Mansi .................... G06T 19/20 345/420 |
| 2015/0302638 A1* | 10/2015 | Jago .................... A61B 8/0866 345/420 |

OTHER PUBLICATIONS

Fischler et al "Random Sample Consensus . . . " Comm. of the ACM, vol. 24, p. 381-395 1981.

* cited by examiner

AUTOMATED SEGMENTATION OF TRI-PLANE IMAGES FOR REAL TIME ULTRASONIC IMAGING

This application is the U.S. National Phase application under 35 U.S.C. § 371 of International Application No. PCT/IB2014/065779, filed on Nov. 4, 2014 which claims the benefit of U.S. Provisional Application No. 61/899,895 filed Nov. 5, 2013. These applications are hereby incorporated by reference herein.

This invention relates to medical ultrasonic imaging systems and, in particular, to 3D ultrasound systems for cardiac imaging.

In cardiac ultrasound imaging there are a number of standard planar views of the heart that must frequently be acquired in order to make standardized measurements or diagnosis of cardiac performance. Three of these standard views are the apical 2-chamber view, the apical 3-chamber view and the apical 2-chamber view, commonly referred to as the AP4, AP3 and AP2 views. As the name connotes, these planar views of the heart are all acquired by holding the ultrasound probe beneath the left rib cage, where it will view the heart from its apex. The apical 4-chamber view visualizes all four chambers of the heart, the left and right atrium and the left and right ventricle. This view is preferred when a clinician wants to calculate ejection fraction, to visualize the left ventricle, or to assess diastolic function or mitral stenosis. The apical 3-chamber view enables the clinician to visualize the aortic valve and the aortic root. This view is preferred for assessing the contractility of the antero-lateral and posterior walls of the heart. By aligning a Doppler beam with the left ventricular outflow tract the clinician is able to quantitatively assess the severity of aortic stenosis. The apical 2-chamber view enables visualization and assessment of the anterior and inferior walls of the left ventricle.

There are familiar and well-understood techniques for manipulating a two-dimensional ultrasound probe in order to acquire these standard planar views of the heart. The 4-chamber view is generally taken as the first view and a reference for the others. To acquire an apical 4-chamber view the clinician holds the probe against the left side of the patient with the probe aimed at the apex of the heart and up toward the right shoulder. The notch on the side of the probe which enables the clinician to maintain a desired left-right orientation between the anatomy of the patient and the image on the ultrasound system display is positioned at 2 or 3 o'clock. When properly positioned the four chambers of the heart are clearly displayed with the apex at the top of the screen and the right chambers on the left side of the screen. The right ventricle should not be larger than two-thirds of the width of the left ventricle.

From the 4-chamber view, acquisition of the apical 3-chamber view requires just a simple manipulation of the probe. The probe is rotated counter-clockwise against the patient until the notch on the probe is at approximately the 11 o'clock position. The 3-chamber view should now be seen on the screen. This rotation means that there is approximately a 90° relationship between the image planes of the 4- and 3-chamber views. To acquire the 2-chamber view the probe is rotated further until approximately the 9 o'clock position. The apical 2-chamber view should now be displayed on the screen. This means that the 2-chamber view is located at a rotation of approximately 135° from the reference 4-chamber view.

As may be gleaned from the foregoing, a clinician can spend a considerable amount of time to acquire these views and manipulate the probe from one view to another. It would be desirable to be able to acquire these standard views of the heart without the careful and painstaking probe manipulation described above. It would further be desirable for the views to be acquired automatically by the ultrasound system with no special manipulation of the probe at all.

In accordance with the principles of the present invention, an ultrasonic imaging system and method are described which enable 3D acquisition of the heart from an apical position. With most of the heart volume acquired in a 3D acquisition, a mathematical heart model is applied by the ultrasound system to the 3D volume to identify and segment three apical view planes of the heart, an AP4, an AP3, and an AP2 image planes. Once segmented, the three image planes are then operated as a tri-plane system to track the tri-plane system in subsequent acquisitions of the 3D volume as a rigid transformation. The tri-plane system can thus be visualized in real time either by extracting MPR slices from live volume images or scanning just the tri-planes with a matrix array transducer probe.

Figure 1:
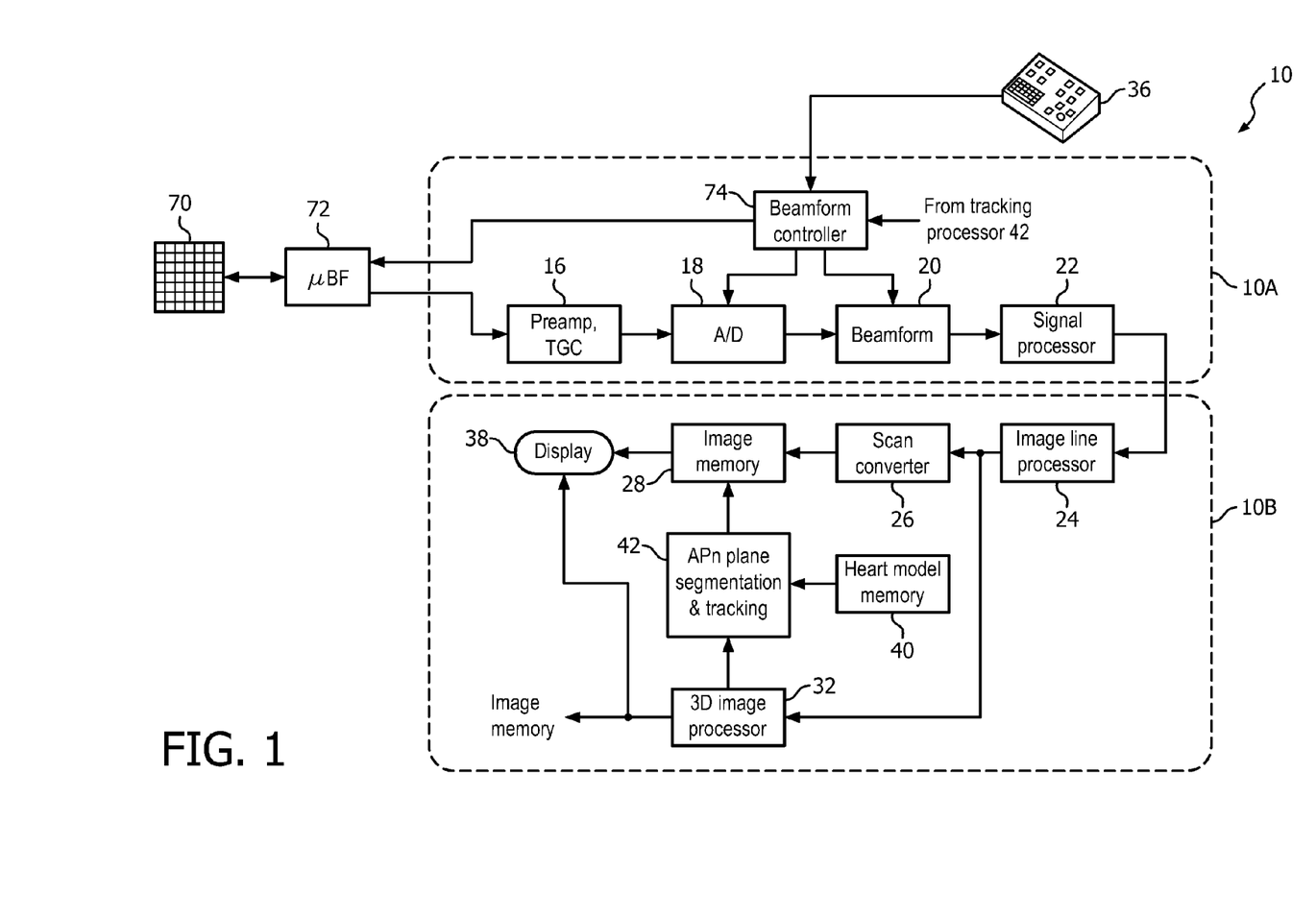
FIG. 1 illustrates in block diagram form a medical ultrasound system constructed in accordance with the principles of the present invention.

Referring first to FIG. 1, an ultrasonic imaging system of the present invention is shown in block diagram form. The ultrasound system is configured by two subsystems, a front end acquisition subsystem 10A and a display subsystem 10B. An ultrasound probe is coupled to the acquisition subsystem which includes a two-dimensional matrix array transducer 70 and a micro-beamformer 72. The micro-beamformer contains circuitry which control the signals applied to groups of elements ("patches") of the array transducer 70 and does some processing of the echo signals received by elements of each group. Micro-beamforming in the probe advantageously reduces the number of conductors in the cable between the probe and the ultrasound system and is described in U.S. Pat. No. 5,997,479 (Savord et al.) and in U.S. Pat. No. 6,436,048 (Pesque).

The probe is coupled to the acquisition subsystem 10A of the ultrasound system. The acquisition subsystem includes a beamform controller 74 which is responsive to a user control 36 and provides control signals to the microbeamformer 72, instructing the probe as to the timing, frequency, direction and focusing of transmit beams. The beamform controller also controls the beamforming of echo signals received by the acquisition subsystem by its control of analog-to-digital (A/D) converters 18 and a system beamformer 20. Echo signals received by the probe are amplified by preamplifier and TGC (time gain control) circuitry 16 in the acquisition subsystem, then digitized by the A/D converters 18. The digitized echo signals are then formed into fully steered and focused beams by the system beamformer 20. The echo signals are then processed by a signal processor 22 which performs digital filtering, B mode and M mode detection, and Doppler processing, and can also perform other signal processing such as harmonic separation, speckle reduction, and other desired image signal processing.

The echo signals produced by the acquisition subsystem 10A are coupled to the display subsystem 10B, which processes the echo signals for display in the desired image format. The echo signals are processed by an image line processor 24, which is capable of sampling the echo signals, splicing segments of beams into complete line signals, and averaging line signals for signal-to-noise improvement or flow persistence. The image lines for a 2D image are scan converted into the desired image format by a scan converter 26 which performs R-theta conversion as is known in the art. The image is then stored in an image buffer or memory 28 from which it can be displayed on a display 38. The image in memory 28 is also overlaid with graphics to be displayed with the image, which are generated by a graphics generator (not shown) which is responsive to the user control 36. Individual images or image sequences can be stored in a cine memory (not shown) during capture of image loops or sequences.

For real-time volumetric imaging the display subsystem 10B also includes a 3D image rendering processor 32 which receives image lines from the image line processor 24 for the rendering of real-time three dimensional images. The 3D images can be displayed as live (real time) 3D images on the display 38 or coupled to the image memory 28 for storage of the 3D data sets for later review and diagnosis.

Figure 2A:
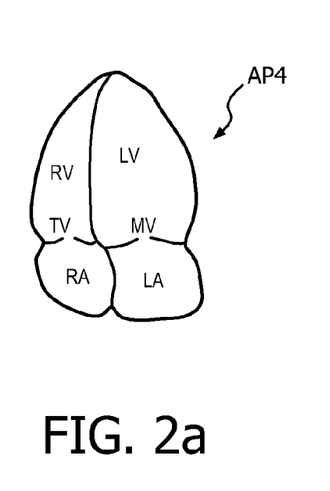
FIGS. 2a, 2b, and 2c are graphical illustrations of AP4, AP3, and AP2 views of the heart.
Figure 2B:
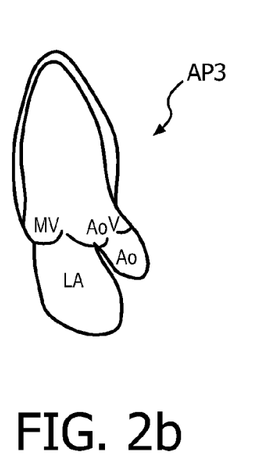
Figure 2C:
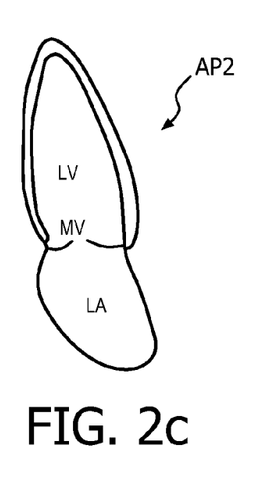
Figure 3:
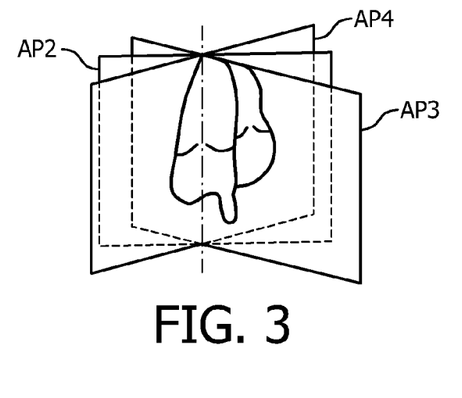
FIG. 3 illustrates the relative orientations of the planes of the AP4, AP3, and AP2 views when arranged in a tri-plane system.

In accordance with the principles of the present invention the display subsystem also includes an analytical geometrical heart model stored in memory 40. The heart model data stored in the memory is conceptually a 3D surface mesh that outlines the shapes of major features of the heart such as fluid chambers, heart valves, and the like. In a constructed embodiment the mesh is made up of interconnected triangular elements, although other meshes such as rectangular or square element meshes or meshes made up of non-uniform rational b-splines may also be used. As contemplated herein, the heart model can be a fully detailed geometric model or simply a model of anatomical landmarks such as chamber walls, heart apex, heart valves or valve plane contours, and the like. A heart model which combines both can also be used. A heart model which identifies the key landmarks of standard planes can be used to identify those standard planes in the ultrasound image data, for instance. The purpose of the heart model is to identify or segment a 3D ultrasound image of a patient's heart. This function is performed by an APn plane segmentation and tracking processor 42 which uses the heart model data to extract certain image planes of the 3D ultrasound image, in this case AP2, AP3, and AP4 image planes. These image planes are shown graphically in FIGS. 2a, 2b and 2c. A model of a four chamber AP4 plane of the heart is shown in FIG. 2a. In this view the clinician can see all four heart chambers, the right atrium and the right ventricle separated by the tricuspid valve, and the left atrium and left ventricle separated by the mitral valve. The apex of the heart is at the top in this orientation of the AP4 model. FIG. 2b illustrates a model of an AP3 three chamber image plane. The AP3 view enables visualization of the left heart chambers as well as the aortic root and the aortic valve. FIG. 2c illustrates an AP2 model. This view enables visualization of the left atrium, the mitral valve and the left ventricle. FIG. 3 is a perspective view of the relative orientations of these three view planes to each other. In a typical exam the clinician will place the ultrasound probe below the left side of the rib cage, aimed up toward the right shoulder. The probe is manipulated until the apical 4 chamber view is acquired. The probe is then tilted upwards to acquire the LV outflow tract and the aortic valve in an apical 3 chamber view or an apical 5 chamber view. The probe is manipulated again by rotating it 90° counterclockwise to acquire the 2 chamber view. It can be appreciated that this is a painstaking and time consuming task, requiring considerable skill by the clinician. The AP2, AP3, and AP4 views are standard view planes for many cardiac diagnoses.

This difficult task and its complexity are obviated by an ultrasound system of the present invention by which the desired apical view planes are extracted from a 3D ultrasound image and displayed by analytical use of a heart model. This extraction is done by the APn plane segmentation and tracking processor 42 which begins by finding the approximate location of the heart model in the 3D ultrasound image volume. A shape finder, implemented in the form of a Hough transform, finds the approximate location of the heart model in the 3D image. A localized affine transform better defines large structures such as the heart fluid chambers in the volume image. Localized fine tuning more precisely aligns the model with the anatomy in the image volume. With the 3D heart model now aligned with the anatomical structure of the heart in the volume image, landmarks of the three apical planes taken from the heart model are used to identify the three planes in the volume image and the three image planes, AP4, AP3, and AP2, are extracted from the volume image.

In an implementation of this processing, the APn plane segmentation and tracking processor 42 operates on voxels of the 3D volume image of the heart as follows. The plane segmentation and tracking processor includes a preprocessor that serves as an initializer for a segmenter. The preprocessor automatically analyses the image data and operates to classify the current view, that is, the view at which the current 3D heart image has been acquired. In other words, the preprocessor is capable of detecting the pose of an organ to be segmented with respect to a reference pose. The "pose" is the position of the object and its orientation with respect to the model as a reference orientation. The detected pose is expressed by "pose parameters". The parameters describe a transformation, that is, how a geometric model of the heart needs to be shifted and rotated so that the so transformed model corresponds to the pose of the heart in the image. Based on these pose parameters, points of the geometric model of the heart are then transformed to the estimated ("current") pose. In a preferred implementation the geometric model of the heart is defined as a 3D surface mesh made up of triangular elements, the mesh roughly outlining a standard heart shape in a given reference pose. The so transformed (that is, shifted and rotated) model is then supplied as a starting point for model based segmentation of the image volume that relies on prior knowledge of the position and orientation of the object to be segmented, in this case, the segmentation of the three desired apical view planes.

The preprocessor utilizes a generalized Hough transform (GHT) with a plurality of accumulators, one for each orientation of the heart. To cope with a range of distinctly varying heart pose possibilities, frequently re-occurring pose orientations are stored in the processor from training 3D images and, after clustering, a set of transformations is computed from those orientations. The transformations are then applied in the operational phase during the GHT voting process to fill the plurality of Hough accumulators. The plurality of Hough accumulators is then searched for the maximum voting entry across all the Hough accumulators to find the instant heart pose. This search may run concurrently across all Hough accumulators or the search may proceed sequentially. The Hough accumulator entry with the highest vote count is taken to represent the most probable object location for a given pose orientation β. In a preferred implementation, extraction of landmarks from the image data is used to determine from a plurality of affine (or other) transformations an optimal transform that best relates to the structures in the instant image. The preprocessor includes an input port for receiving the 3D image and a classifier. There is also an output port for outputting the pose parameters (β[=orientation], x[=position]) of the pose as determined by the classifier. This pose information (β, x) may then be applied to the geometric heart model. The transformed model forms the "initialized model" for segmentation. The segmenter, once the pose of the heart in the to-be-segmented image is known (that is, the initialized model is available) applies parameterized and deformable adaptation steps to the geometric heart model. The model is thereby adapted to the structure of the heart in the instant image volume. Specifically, the adaptations include one or more stages where the model's coordinates are adapted to the volume image data by applying successively a global rigid, a global affine, a multi-rigid, and a deformable transformation. After deforming the initialized model, grey value intensities across normals of the mesh model's triangular faces are evaluated to define the boundaries of the segmentation.

When anatomical landmark identification is used for heart model registration and image plane extraction, a landmark identifier operates to detect/identify one or more anatomic landmarks in the 3D heart image. Landmark detection in the image may be based on the RANSAC (Random Sample Consensus) algorithm as described in M. Fischler et al's "Random Sample Consensus . . . ", Communications of the ACM, Volume 24(6), (1981.) The collection of the so-detected landmarks may then be taken to represent a skeleton of the underlying geometric model of the heart when assumed to be in a certain pose. The heart model includes landmark target points representing the landmarks therein. In this implementation, operation of the classifier is based on a collection of affine transformations Ti. The transformations Ti are applied one by one to the detected landmark points to effect a coordinate transformation of the detected landmarks. The so-transformed landmarks can then be compared with the reference geometric model. In particular, the transformed landmark points in the image are compared with the target landmark points of the heart model. The model is assumed to be presented with respect to a reference orientation. For each transformation, the coordinates of the transformed landmarks are then compared with the coordinates of the landmarks target points of the model. The coordinates of the transformed landmarks that fit best (for instance, are closest to with respect to a suitable norm) the target point landmarks of the model are then identified. The respective transformation that yields the best fit or match between transformed landmark points and target landmark points is then considered to represent the pose as recorded in the underlying heart volume image. The "best" fit is established with respect to a similarity measure. "Best" is meant to include being within a user definable margin rather being closest in the arithmetical sense, although a particular implementation may indeed envisage "best" to mean proximal in the arithmetical sense. Computing the best fit with respect to a pre-set margin allows efficient processing because the processor need not cycle through all pre-defined transformations to evaluate the similarity measure. As soon as a similarity value that lies within the margin has been established, the output unit returns the respective transformation as the "best fit".

Each of the predefined affine transformations can be thought to encode a certain pose. In particular, each affine transformation includes among other components (such as shearing) a translation and a rotation component that describe a respective one of the poses. A description of the translation and rotation components of the identified best fit transformation is forwarded to the segmenter for initialization. Alternatively, the best-fit transformation is directly applied to the model first, and it is the so-transformed model that is then forwarded to initialize the segmenter. The segmenter performs the now straightforward task of identifying landmark target points of the three desired apical planes and extracts from the image volume the three planes which most completely contain those anatomical landmarks.

Figures 5A, 5B, 5C:
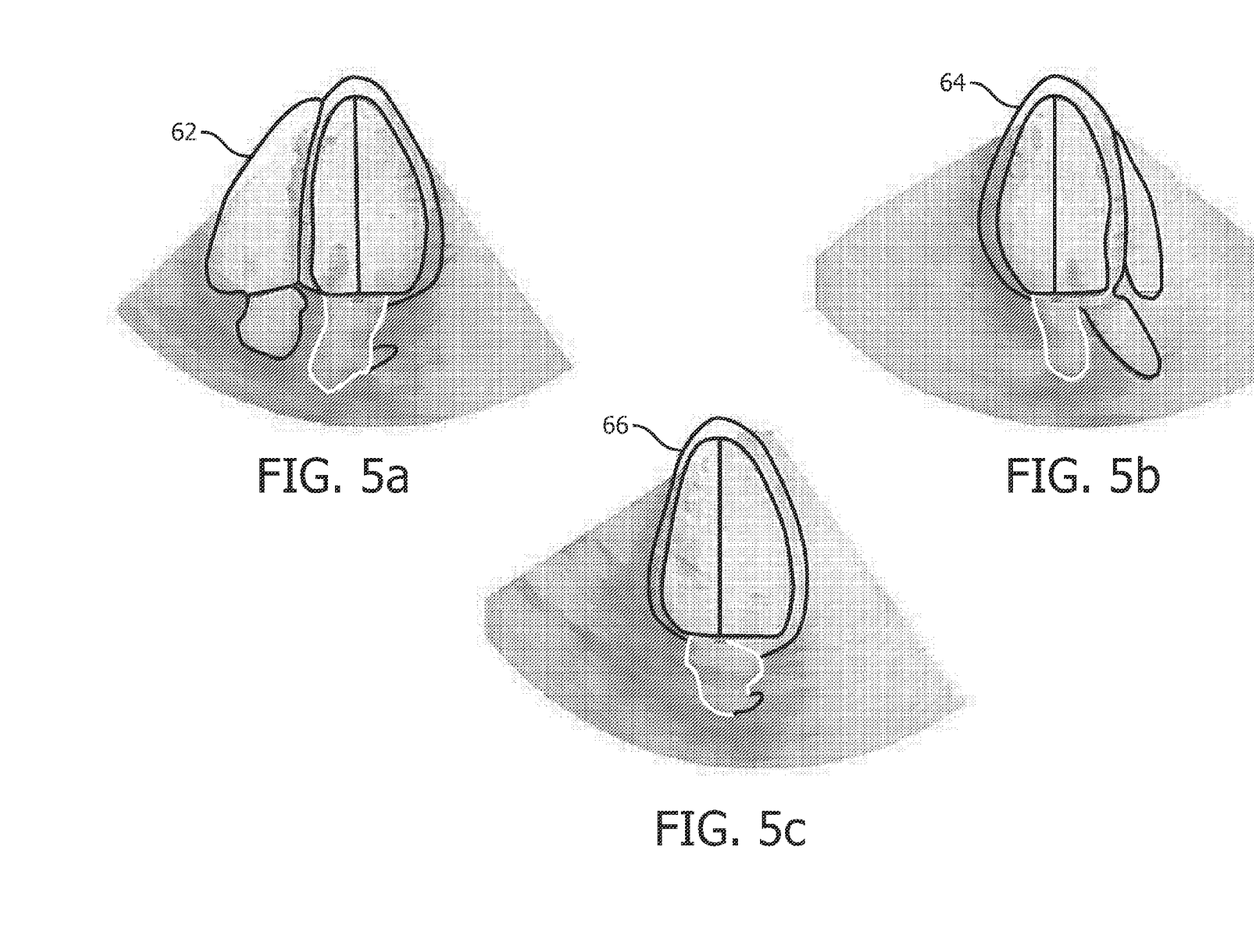
FIGS. 5a, 5b, and 5c illustrate three ultrasound images of an apical tri-plane system as they appear when viewed simultaneously as live images on an ultrasound display screen and when overlaid by graphics representing the view planes of a heart model.

The three apical view planes extracted from the 3D heart image data by the APn plane segmentation and tracking processor 42 as described above are individually or concurrently displayed on the ultrasound system display 38 as illustrated in FIG. 5*a* (of the 4-chamber view), FIG. 5*b* (of the 3-chamber view) and FIG. 5*c* (of the 2-chamber view). In the illustrated implementation the chambers and structures of the heart of each image plane are segmented by an overlay of graphically delineated anatomical borders 62, 64, 66 provided by the heart model. Once this has been done for one volume image the APn planes can be tracked through successive image volumes, either in real time or in post-processing. For tracking, the three planes are not treated as unrelated image planes but as three planes of a tri-plane system as illustrated in FIG. 3. As successive heart volume images become available the three APn planes of the heart model are used to extract the three image planes from each successive volume image. Those planes are tracked in the new volume by analyzing the gross motion of the anatomical landmarks from the previous tri-plane system to the newly identified tri-plane system. This is done by optical flow or image registration such as by use of mutual information, block matching or feature matching, for instance. The motion of the landmarks from one plane to the next is used to find a motion vector for each plane and the three motion vectors of the three planes are used to determine a composite motion vector (transformation) of the tri-plane system. In essence, the three in-plane motion vectors are used to identify the composite motion of the tri-plane system. This transformation is used to model the motion of the tri-plane system as a rigid transformation relative to the probe. The rigid transformation identifies the translation and rotation of the tri-plane system from one volume image to the next and this displacement is used to compute the new location of the tri-plane system in the new volume image. Since this is a rigid transformation there is no scaling or warping of the model or image data which eases the computational demands. This tracking and tri-plane system updating is repeated for each new volume image acquisition. Occasionally, to guard against excessive heart or probe motion, the processing can be re-initialized as described above.

Figure 4:
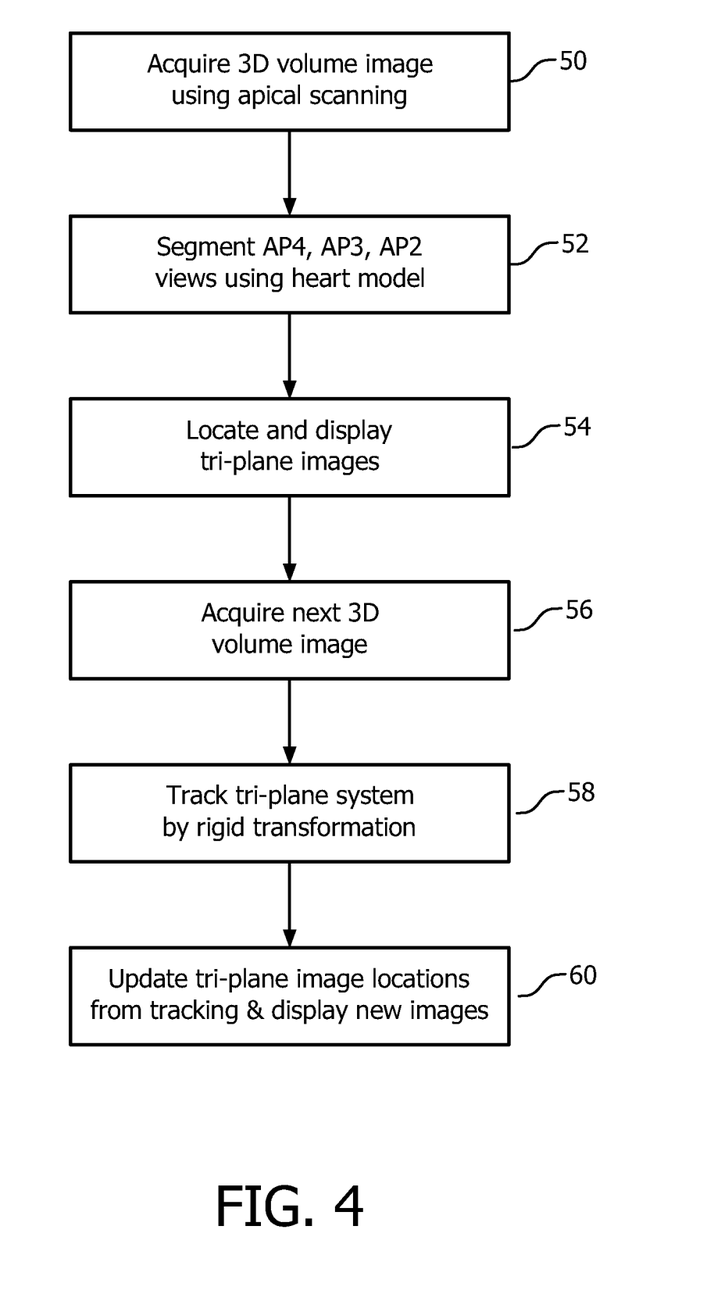
FIG. 4 is a flowchart of the acquisition, segmentation, and tracking of an apical tri-plane image system in accordance with the principles of the present invention.

FIG. 4 illustrates a typical sequence of reference plane segmentation and tracking in accordance with the principles of the present invention. In the first step 50, a 3D volume image of the heart is acquired by apical scanning. Since the heart is scanned apically, the APn plane segmentation and tracking processor 42 can be preconditioned to expect to find the apex of the heart at the top of the volume image. In step 52 the the APn plane segmentation and tracking processor 42 segments the AP4, AP3, and AP2 view planes using the heart model to identify the pose of the heart and fits the heart model to the 3D image data as described above. In step 54 the processor uses the desired plane locations of the fitted the heart model to extract and display the tri-plane images. In step 56 a new 3D volume image is acquired and in step 58 the tri-plane system in the new volume image is tracked by rigid transformation. In step 60 the tracked tri-plane system images are extracted from the new image data and the displayed tri-plane images are updated on the display.

Other variations of the invention will readily occur to those skilled in the art. Instead of extracting and displaying the AP4, AP3 and AP2 views, other view may alternatively or additionally be acquired and displayed. The ultrasound system may be used to display AP4, AP5 and AP3 views, for instance, or four different view planes. For higher frame rates of display the tracking information may be used to update the planes of a tri-plane display which only scans the three desired view planes and not an entire volume each time. For example, after the heart model has been fitted to the heart anatomy in a volume image, only the tri-planes can be scanned for the next update. Three newly scanned image planes can be compared with the previous tri-planes and the computed composite motion data (tracking data) used to scan the tri-planes at the updated plane locations for display. The tracking data is thus used to steer the direction of plane scanning of the next tri-plane acquisition by control of the beamform controller as shown in FIG. 1. By only scanning three planes instead of the entire heart volume, the frame rate and spatial resolution of display are improved considerably. Should the gross motion of the heart or probe become excessive, the process can be updated and re-initialized by acquiring and processing a new volume image and the tri-plane scanning commenced again. As another alternative, the 3D image data can be transformed to fit the heart model instead of the reverse for segmentation.

What is claimed is:

1. An ultrasonic diagnostic imaging system which acquires a plurality of standard view planes of a heart comprising:
    a matrix array probe configured to acquire a 3D volume image data of the heart;
    a memory comprising data of a geometrical heart model;
    a segmentation and tracking processor configured to:
        automatically register the heart image data and the heart model;
        determine an initial orientation of the heart model based on the heart image data;
        generate a fitted heart model by transforming the heart model to fit the heart image data based on the determined initial orientation; and
        segment from the heart image data a plurality of predetermined view planes that are determined based on key landmarks in the heart model, wherein an orientation of each of the plurality of predetermined view planes is determined relative to the fitted heart model; and
    an image display that is responsive to the segmentation and tracking processor and configured to display images of the plurality of view planes,
    wherein the segmentation and tracking processor is further operable to track acquisition of successive images of the plurality of view planes for updating of the displayed images.

2. The ultrasonic diagnostic imaging system of claim 1, wherein the segmentation and tracking processor is configured to track the plurality of view planes as a multi-plane system.

3. The ultrasonic diagnostic imaging system of claim 2, wherein the plurality of predetermined view planes further comprise three image planes; and wherein the segmentation and tracking processor is configured to track the three image planes as a tri-plane system.

4. The ultrasonic diagnostic imaging system of claim 3, wherein the three image planes further comprise an AP4 view plane, an AP3 view plane, and an AP2 view plane.

5. The ultrasonic diagnostic imaging system of claim 2, wherein the segmentation and tracking processor is configured to track the plurality of view planes by rigid transformation.

6. The ultrasonic diagnostic imaging system of claim 5, wherein the plurality of predetermined view planes further comprise three image planes; and wherein the segmentation and tracking processor is configured to track the three image planes as a tri-plane system.

7. The ultrasonic diagnostic imaging system of claim 1, wherein the segmentation and tracking processor is configured to track the plurality of predetermined view planes through a plurality of successively acquired 3D heart images.

8. The ultrasonic diagnostic imaging system of claim 1, wherein the segmentation and tracking processor is configured to track the plurality of predetermined view planes by controlling a scan direction of successively acquired image planes.

9. The ultrasonic diagnostic imaging system of claim 1, wherein the segmentation and tracking processor is further operable to periodically update registration of heart image data and heart model data.

10. A method for acquiring a plurality of standard view plane of a heart comprising:
    acquiring 3D volume image data of the heart with a matrix array probe;
    registering the image data of the heart with data of a geometrical heart model stored in memory;
    determining an initial orientation of the heart model based on the heart image data;
    generating a fitted heart model by transforming the heart model to fit the heart image data based on the determined initial orientation;
    segmenting from the heart image data a plurality of predetermined view planes that are determined based on key landmarks in the heart model, wherein an orientation of each of the plurality of predetermined view planes is determined relative to the fitted heart model;
    displaying images of the plurality of view planes on an image display; and
    tracking acquisition of successive images of the plurality of view planes for updating of the displayed images.

11. The method of claim 10, further comprising tracking the plurality of view planes as a multi-plane system.

12. The method of claim 11, wherein the multiplane system is tracked by rigid transformation.

13. The method of claim 10, further comprising: successively acquiring 3D volume image data; and tracking the plurality of view planes in the successively acquired 3D volume image data.

14. The method of claim 10, further comprising steering the direction of scan planes in successive acquisition intervals.

15. The method of claim 14, further comprising periodically updating registration of heart image data with data of the geometrical heart model.

16. The ultrasonic diagnostic imaging system of claim 1, wherein the heart model comprises a 3D geometric surface mesh.

17. The ultrasonic diagnostic imaging system of claim 16, wherein the 3D geometric surface mesh comprises a plurality of triangular elements.

18. The ultrasonic diagnostic imaging system of claim 3, wherein a first and a second view plane of the plurality of view planes are spaced approximately 90 degrees apart, wherein the second and a third view plane of the plurality of view planes are spaced approximately 135 degrees apart.

19. The ultrasonic diagnostic imaging system of claim 1, wherein the matrix array probe comprises a two-dimensional array.

20. The ultrasonic diagnostic imaging system of claim 1, wherein at least two of the plurality of predetermined view planes intersect along a line passing through the heart model.

* * * * *